United States Patent [19]

Liversidge et al.

[11] Patent Number: 5,399,363
[45] Date of Patent: Mar. 21, 1995

[54] SURFACE MODIFIED ANTICANCER NANOPARTICLES

[75] Inventors: Gary G. Liversidge; Elaine Liversidge, both of West Chester; Pramod P. Sarpotdar, Malvern, all of Pa.

[73] Assignee: Eastman Kodak Company, Rochester, N.Y.

[21] Appl. No.: 908,125

[22] Filed: Jul. 1, 1992

Related U.S. Application Data

[63] Continuation-in-part of Ser. No. 647,105, Jan. 25, 1991, Pat. No. 5,145,684.

[51] Int. Cl.$^6$ .............................................. A61K 9/14
[52] U.S. Cl. ................................... 424/490; 424/489
[58] Field of Search ................. 424/490, 487; 514/352

[56] References Cited

U.S. PATENT DOCUMENTS

| | | | |
|---|---|---|---|
| 2,671,750 | 3/1954 | Macek | 514/179 |
| 3,881,020 | 4/1975 | Nakamura et al. | 514/619 |
| 4,107,288 | 8/1978 | Oppenheim | 424/22 |
| 4,225,581 | 9/1980 | Kreuter et al. | 424/88 |
| 4,269,821 | 5/1981 | Kreuter et al. | 424/489 |
| 4,540,602 | 9/1985 | Motoyama | 427/213.31 |
| 4,826,689 | 5/1989 | Violanto | 424/489 |
| 4,851,421 | 7/1989 | Iwasaki et al. | 514/352 |
| 5,049,322 | 9/1991 | Devissaguet | 424/490 |
| 5,091,188 | 2/1992 | Haynes | 424/450 |
| 5,118,525 | 6/1992 | Fessi | 424/487 |
| 5,124,338 | 6/1992 | King | 514/352 |

FOREIGN PATENT DOCUMENTS

| | | |
|---|---|---|
| 262560 | 9/1987 | European Pat. Off. . |
| 411629 | 2/1991 | European Pat. Off. . |
| 499299 | 1/1992 | European Pat. Off. . |
| 2118987 | 4/1972 | France . |
| 3772837 | 7/1987 | Germany . |
| 2282330 | 11/1990 | Japan . |
| 2185397 | 7/1987 | United Kingdom . |
| 2200048 | 7/1988 | United Kingdom . |
| 8400294 | 7/1983 | WIPO . |
| 9115193 | 6/1989 | WIPO . |
| 9015593 | 6/1990 | WIPO . |
| 9203380 | 8/1990 | WIPO . |
| 9106292 | 11/1990 | WIPO . |

OTHER PUBLICATIONS

Lachman et al., "The Theory and Practice of Industrial Pharmacy", Chapter 2 (1986).
Remington's Pharmaceutical Sciences, 17th Edition, Chapter 20, Schott, H., "Colloidal Dispersions".
Goodman and Gilman, "The Pharmacological Basis of Therapeutics", Eighth Edition, pp. 68–69.

*Primary Examiner*—Thurman K. Page
*Assistant Examiner*—William E. Benston, Jr.
*Attorney, Agent, or Firm*—Arthur H. Rosenstein

[57] ABSTRACT

Dispersible particles consisting essentially of a crystalline anticancer agent having a surface modifier adsorbed on the surface thereof in an amount sufficient to maintain an effective average particle size of less than about 1000 nm. Anticancer compositions comprising the particles exhibit reduced toxicity and/or enhanced efficacy, and can be administered by IV bolus injection.

17 Claims, No Drawings

SURFACE MODIFIED ANTICANCER NANOPARTICLES

CROSS REFERENCED TO RELATED APPLICATION

This application is a continuation-in-part of U.S. patent application Ser. No. 647,105, filed Jan. 25, 1991, now U.S. Pat. No. 5,145,684, the disclosure of which is hereby incorporated by reference in its entirety.

BACKGROUND OF THE INVENTION

1. Field of Invention

This invention relates to anticancer agents in the form of particles, to anticancer compositions comprising the particles, and to methods employing the particles.

2. Description of the Prior Art

The therapeutic index is a measure of how selective a drug is at producing its desired effects and can be defined as the ratio of the median lethal dose to the median effective dose, i.e., ($LD_{50}/ED_{50}$) (see Goodman and Gilman, *The Pharmacological Basis of Therapeutics*, Eight Edition, p. 68–69). Virtually all anticancer agents have a low therapeutic index, e.g., less than about 1.0. Increasing the therapeutic index, e.g., by reducing toxicity or enhancing efficacy would provide more latitude to physicians in their duty of administering anticancer drugs to patients in need thereof. Consequently, methods to reduce toxicity and/or enhance efficacy of anticancer drugs and thus increase the therapeutic indices of such drugs would be of great value in the treatment of cancers.

In addition, poorly water-soluble drugs, such as poorly water-soluble anticancer agents, are not readily injectable via an intravenous (IV) bolus injection. The creation of injectable forms of poorly soluble drugs represents a formidable problem. It would be highly desirable to be able to provide poorly soluble drugs, such as poorly soluble anticancer agents, in an IV bolus injectable form.

SUMMARY OF THE INVENTION

We have discovered that anticancer compositions comprising anticancer agents in the form of surface modified nanoparticles exhibit reduced toxicity and/or enhanced efficacy.

More particularly, in accordance with this invention, there are provided particles consisting essentially of a crystalline anticancer agent having a surface modifier adsorbed on the surface thereof in an amount sufficient to maintain an effective average particle size of less than about 1000 nm.

This invention further provides an anticancer composition comprising the above-described particles.

In another embodiment of the invention, there is provided a method of treating a mammal comprising administering to the mammal the above-described anticancer composition.

In yet another embodiment of the invention, there is provided a method of enhancing the efficacy and/or reducing the toxicity of an anticancer agent which includes the step of administering the agent in the form of the above-described particles.

It is an advantageous feature of this invention that anticancer compositions are provided exhibiting reduced toxicity.

It is another advantageous feature of this invention that anticancer compositions are provided exhibiting improved efficacy.

Yet another advantageous feature of this invention is that compositions are provided featuring poorly soluble anticancer agents that can be administered by IV bolus injection.

Still another advantageous feature of this invention is that compositions are provided containing poorly soluble anticancer agents exhibiting prolonged circulation in the blood pool after IV bolus injection.

Other advantageous features will become readily apparent upon reference to the following descriptions of preferred embodiments.

DESCRIPTION OF PREFERRED EMBODIMENTS

This invention is based partly on the discovery that surface modified anticancer nanoparticles exhibit reduced toxicity and/or enhanced efficacy. While the invention is described herein primarily in connection with its preferred class of drugs, i.e., anticancer agents including immunosuppressive agents, it is also useful in conjunction with poorly water soluble drugs, particularly those with low therapeutic indices, from other classes of drug substances.

The particles of this invention comprise an anticancer agent. The anticancer agent is present in one or more discrete crystalline phases. The crystalline phase differs from an amorphous, i.e., non-crystalline phase which results from conventional solvent precipitation techniques for the preparation of particles in the submicron size range, such as described in U.S. Pat. No. 4,826,689.

The invention can be practiced with a wide variety of anticancer agents. However, the anticancer agent must be poorly soluble and dispersible in at least one liquid medium. By "poorly soluble", it is meant that the drug substance has a solubility in the liquid dispersion medium, e.g., water, of less than about 10 mg/ml, preferably, of less than 1 mg/ml at processing temperature, e.g., room temperature. The preferred liquid dispersion medium is water. However, the invention can be practiced with other liquid media in which the anticancer agent is dispersible including, for example, aqueous salt solutions, safflower oil, and solvents such as ethanol, t-butanol, hexane, and glycol. The pH of the aqueous dispersion media can be adjusted by techniques known in the art.

The anticancer agent preferably is selected from alkylating agents, antimetabolites, natural products, hormones and antagonists, and miscellaneous agents, such as radiosensitizers.

Examples of alkylating agents include alkylating agents having the bis-(2-chloroethyl)-amine group such as, for example, chlormethine, chlorambucile, melphalan, uramustine, mannomustine, extramustinephoshate, mechlore-thaminoxide, cyclophosphamide, ifosfamide, and trifosfamide;

alkylating agents having a substituted aziridine group such as, for example, tretamine, thiotepa, triaziquone and mitomycine;

alkylating agents of the alkyl sulfonate type, such as, for example, busulfan, piposulfan, and piposulfam;

alkylating N-alkyl-N-nitrosourea derivatives, such as, for example, carmustine, lomustine, semustine, or streptozotocine; and alkylating agents of the mitobronitole, dacarbazine and procarbazine type.

Examples of antimetabolites include folic acid analogs, such as, for example, methotrexate;

pyrimidine analogs such as, for example, fluorouracil, floxuridine, tegafur, cytarabine, idoxuridine, and flucytosine; and purine derivatives such as, for example, mercaptopurine, thioguanine, azathioprine, tiamiprine, vidarabine, pentostatin, and puromycine.

Examples of natural products include vinca alkaloids, such as, for example, vinblastine and vincristine;

epipodophylotoxins, such as, for example, etoposide and teniposide;

antibiotics, such as, for example, adriamycine, daunomycine, doctinomycin, daunorubicin, doxorubicin, mithramycin, bleomycin, and mitomycin;

enzymes, such as, for example, L-asparaginase;

biological response modifiers, such as, for example, α-interferon;

camptothecin;

taxol; and retinoids, such as retinoic acid.

Examples of hormones and antagonists include adrenocorticosteroids, such as, for example, prednisone;

progestins, such as, for example, hydroxyprogesterone caproate, medroxyprogesterone acetate and megestrol acetate;

estrogens, such as, for example, diethylstilbestrol and ethinyl estradiol;

antiestrogens, such as, for example, tamoxifen;

androgens, such as, for example, testosterone propionate and fluoxymesterone;

antiandrogens, such as, for example, flutamide;

and gonadotropin-releasing hormone analogs, such as, for example leuprolide.

Examples of miscellaneous agents include radiosensitizers, such as, for example, 1,2,4-benzotriazin-3-amine 1,4-dioxide (SR 4889) and 1,2,4-benzotriazine-7-amine 1,4-dioxide (WIN 59075);

platinum coordination complexes such as cisplatin and carboplatin;

anthracenediones, such as, for example, mitoxantrone;

substituted ureas, such as, for example, hydroxyurea;

and adrenocortical suppressants, such as, for example, mitotane and aminoglutethimide.

In addition, the anticancer agent can be an immunosuppressive drug, such as, for example, cyclosporine, azathioprine, sulfasalazine, methoxsalen and thalidomide.

The anticancer agents useful in the practice of this invention are known compounds and/or can be prepared by techniques known in the art.

The anticancer agent can be used alone or in combination with one or more anticancer agents.

The particles of this invention contain an anticancer agent as described above having a surface modifier adsorbed on the surface thereof. Useful surface modifiers are believed to include those which physically adhere to the surface of the anticancer agent but do not chemically bond to the anticancer agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens TM, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol (PVA), and polyvinylpyrrolidone (PVP). Most of these excipients are described in detail in the *Handbook of Pharmaceutical Excipients,* published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

Particularly preferred surface modifiers include polyvinylpyrrolidone, tyloxapol, polaxomers, such as Pluronic TM F68, F108 and F127, which are block copolymers of ethylene oxide and propylene oxide available from BASF, and poloxamines, such as Tetronic TM 908 (T908), which is a tetrafunctional block copolymer derived from sequential addition of ethylene oxide and propylene oxide to ethylenediamine available from BASF, dextran, lecithin, Aerosol OT TM (AOT), which is a dioctyl ester of sodium sulfosuccinic acid, available from American Cyanamid, Duponol TM P, which is a sodium lauryl sulfate, available from DuPont, Triton TM X-200, which is an alkyl aryl polyether sulfonate, available from Rohm and Haas, Tween 20, 40, 60 and 80, which are polyoxyethylene sorbitan fatty acid esters, available from ICI Speciality Chemicals, Span 20, 40, 60 and 80, which are sorbitan esters of fatty acids, Arlacel 20, 40, 60 and 80, which are sorbitan esters of fatty acids, available from Hercules, Inc., Carbowax TM 3550 and 934, which are polyethylene glycols available from Union Carbide, Crodesta TM F-110, which is a mixture of sucrose stearate and sucrose distearate, available from Croda Inc., Crodesta SL-40, which is available from Croda, Inc., hexyldecyl trimethyl ammonium chloride (CTAC), bovine serum albumin and SA90HCO, which is $C_{18}H_{37}$ $CH_2$ (CON $(CH_3)$ $CH_2$ $(CHOH)_4CH_2OH)_2$. Surface modifiers which have been found to be particularly useful include polyvinylpyrrolidone, Pluronic F-108, polyvinyl alcohol and gum acacia.

The surface modifier is adsorbed on the surface of the anticancer agent in an amount sufficient to maintain an effective average particle size of less than about 1000 nm. The surface modifier does not chemically react with the anticancer agent or itself. Furthermore, the individually adsorbed molecules of the surface modifier are essentially free of intermolecular crosslinkages.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 1000 nm" it is meant that at least 90% of the particles have a number average particle size of less than about 1000 nm when measured by the above-noted techniques. In particularly preferred embodiments of the invention, the effective average particle size is less than about 400 nm. In some embodiments of the invention, the effective average particle size is less than about 300 nm. With reference to the effective average particle size, it is preferred that at least 95% and, more preferably, at least 99% of the particles have a particle size of less than the effective average, e.g., 1000 nm. In particularly preferred embodiments, essentially all of the particles have a size less than 1000 nm.

Motoyama et al, U.S. Pat. No. 4,540,602 disclose that a solid drug can be pulverized in an aqueous solution of a water-soluble high molecular substance, and that as a result of such wet grinding, the drug is formed into finely divided particles ranging from 0.5 μm or less to 5 μm in diameter. However, there is no suggestion that particles having an average particle size of less than about 1 μm can be obtained. Attempts to reproduce the wet grinding procedures described by Motoyama et al resulted in particles having an average particle size of much greater than 1 μm.

The particles of this invention can be prepared by a method comprising the steps of dispersing an anticancer agent in a liquid dispersion medium and applying mechanical means in the presence of grinding media to reduce the particle size of the anticancer agent to an effective average particle size of less than about 1000 nm. The particles can be reduced in size in the presence of a surface modifier. Alternatively, the particles can be contacted with a surface modifier after attrition.

A general procedure for preparing the particles of this invention is set forth below. The anticancer agent selected is obtained commercially and/or prepared by techniques known in the art in a conventional coarse form. It is preferred, but not essential, that the particle size of the coarse anticancer agent selected be less than about 100 μm as determined by sieve analysis. If the coarse particle size of the anticancer agent is greater than about 100 μm, then it is preferred that the particles of the anticancer agent be reduced in size to less than 100 μm using a conventional milling method such as airjet or fragmentation milling.

The coarse anticancer agent selected can then be added to a liquid medium in which it is essentially insoluble to form a premix. The concentration of the anticancer agent in the liquid medium can vary from about 0.1–60% and preferably is from 5–30% (w/w). It is preferred, but not essential, that the surface modifier be present in the premix. The concentration of the surface modifier can vary from about 0.1 to about 90% and preferably is 1–75%, more preferably 20–60%, by weight based on the total combined weight of the drug substance and surface modifier. The apparent viscosity of the premix suspension is preferably less than about 1000 centipoise.

The premix can be used directly by subjecting it to mechanical means to reduce the average particle size in the dispersion to less than 1000 nm. It is preferred that the premix be used directly when a ball mill is used for attrition. Alternatively, the anticancer agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the anticancer agent conveniently can take the form of a dispersion mill. Suitable dispersion mills include a ball mill, an attritor mill, a vibratory mill, a planetary mill, media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, zirconium oxide, such as 95% ZrO stabilized with magnesia, zirconium silicate, and glass grinding media provide particles having levels of contamination which are believed to be acceptable for the preparation of pharmaceutical compositions. Further, other media, such as stainless steel, titania, alumina, and 95% ZrO stabilized with yttrium, are expected to be useful. Preferred media have a density greater than about 2.5 g/cm$^3$.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the anticancer agent. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

The surface modifier, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of the anticancer agent and surface modifier can vary widely and the optimal amount of the surface modifier can depend, for example, upon the particular anticancer agent and surface modifier selected, the critical micelle concentration of the surface modifier if it forms micelles, the surface area of the anticancer agent, etc. The surface modifier preferably is present in an amount of about 0.1–10 mg per square meter surface area of the anticancer agent. The surface modifier can be present in an amount of 0.1–90%, preferably 0.5–80% and more preferably 1–60% by weight based on the total weight of the dry particle.

A simple screening process has been developed whereby compatible surface modifiers and anticancer agents can be selected which provide stable dispersions of the desired particles. First, coarse particles of an anticancer agent are dispersed in a liquid in which the anticancer agent is essentially insoluble, e.g., water at 2% (w/v) and milled for 120 hours in a roller mill under the following milling conditions:

Grinding vessel: 8 oz. (250 ml) glass jar
Available volume of grinding vessel: 250 ml
Media volume: 120 ml
Media type: 1.0 mm pre-cleaned zirconium oxide beads (distributed by Zircoa, Inc.)
Milling time: 120 hours
Slurry volume: 60 ml
RPM: 92
Room Temperature The slurry is separated from the milling media by conventional means, e.g., by pouring the slurry out of the vessel, or by using a pipette. The separated slurry is then divided into aliquots and surface modifiers are added at a concentration of between 2 and 50% by weight based on the total combined weight of the anticancer agent and surface modifier. The dispersions are then sonicated (1 minute, 20 kHz) or vortexed using a multitubed vortexer for one minute, to disperse agglomerates and subjected to particle size analysis, e.g., by photon correlation spectroscopy (PCS) and/or by examination under an optical microscope (1000×magnification). If a stable dispersion is observed, then the process for preparing the particular anticancer agent surface modifier combination can be optimized in accordance with the teachings above. By stable it is meant that the dispersion exhibits no flocculation or particle agglomeration visible to the naked eye and, preferably, when viewed under the optical microscope at 1000×, at least 15 minutes, and preferably, at least two days or longer after preparation. In addition, preferred particles exhibit no flocculation or agglomeration when dispersed in 0.1N HCl and/or phosphate buffered saline, pH 7.4 (PBS) or rat plasma.

The resulting dispersion is stable and consists of the liquid dispersion medium and the above-described particles. The dispersion of surface modified anticancer agent nanoparticles can be spray coated onto sugar spheres or onto a pharmaceutical excipient in a fluid-bed spray coater by techniques well known in the art.

Anticancer pharmaceutical compositions according to this invention include the particles described above and a pharmaceutically acceptable carrier therefor. Suitable pharmaceutically acceptable carriers are well known to those skilled in the art. These include non-toxic physiologically acceptable carriers, adjuvants or vehicles for parenteral injection, for oral administration in solid or liquid form, for rectal administration, nasal administration, intramuscular administration, subcutaneous administration, and the like.

A method of treating a mammal in accordance with this invention comprises the step of administering to the mammal in need of treatment an effective amount of the above-described anticancer composition. The selected dosage level of the anticancer agent for treatment is effective to obtain a desired therapeutic response for a particular composition and method of administration.

The selected dosage can be readily determined by one skilled in the art and depends upon the particular anticancer agent, the desired therapeutic effect, the route of administration, the desired duration of treatment and other factors.

It is a particularly advantageous feature that the anticancer compositions of this invention exhibit reduced toxicity and/or enhanced efficacy as illustrated in the examples that follow. Further, the particles of this invention exhibit prolonged circulation in the blood pool.

Moreover, anticancer agents which heretofore could not be administered by injection, when prepared as nanoparticles and formulated in anticancer compositions according to this invention, can be effectively administered by injection, e.g., by an intravenous bolus injection.

The following examples further illustrate the invention.

EXAMPLES 1–4 Nanoparticulate Piposulfan

EXAMPLE 1

Piposulfan (purchased from Eastman Kodak) was milled in a mixture of 0.33% polyoxyethylene sorbitan monooleate, Tween 80, (ICI Americas, Inc., Wilmington, Del.) and 0.67% sorbitan monooleate, Span 80, (ICI) using 1 mm zirconium oxide beads for about 96 hours to produce particles approximately 240 nm in diameter. The final piposulfan concentration in the suspension was 10 mg/mL. The particles were stable to flocculation/aggregation in rat plasma.

Milling Conditions: A coarse suspension of piposulfan was prepared by adding 300 mg of the drug to a 4 oz. (120 mL) amber bottle which was previously filled with 60 mL of 1 mm precleaned zirconium oxide beads (Zircoa Inc., Solon, Ohio) and 30 mL of 1% Tween 80/Span 80 (1 to 2 ratio) solution. The surfactant solution was prepared by accurately weighing 333 mg of Tween 80 and 667 mg of Span 80 in a volumetric flask followed by addition of sterile water for injection to dissolve/disperse the surfactants. Sufficient quantity of water was added to make the final volume 100 mL. Zirconium oxide beads were cleaned by first rinsing in 1N sulfuric acid followed by several rinses with deionized water. The media was dried in a vacuum oven at about 100° C. overnight.

The sealed primary container was loaded into a secondary padded aluminium containment can to ensure a tight fit. It was milled on a roller mill (US Stoneware, Mawah, N.J.) at 144 RPM for about 96 hours. At the end of the milling time the slurry was separated from the media and particle size was measured using a PCS device. Stability of these particles to rat plasma was assessed by optical microscopy at 1000×magnification. The final pH of the formulation was 6.

Control A (unmilled), a coarse suspension containing 40 mg of bulk piposulfan was dispersed in water in the presence of 3% ethanol and 1% Tween 80. This suspension could not be injected IV.

Example 1 was evaluated for efficacy studies in female mice (avg. wt. 22 g) which were implanted with early stage Mammary Adenocarcinoma #16/C on day 0. The formulation was injected starting from day 1 for several days. The antitumor activity was assessed by monitoring tumor weight and comparing it to the control animals. The results were as follows:

| Treatment | Route of Adm.* | Total Dose (mg/kg) | % Wt. Loss | T/C % | Log10 Cell Kill |
|---|---|---|---|---|---|
| Control | — | — | +5.5 | — | — |
| Example 1 | IV | 356 | −5.5 | 0 | 2.75 |
| (243 nm) | IV | 220 | −5.5 | 2 | 2.75 |
| | IV | 137 | −1.8 | 2 | 2.25 |
| | IV | 85 | 0 | 18 | 1.0 |
| Control A | SC | 800 | −10.8 | 0 | 2.1 |

*Administration - IV Intravenous; SC Subcutaneous
Example 1 could be injected directly as 10 mg/ml suspension. There was no acute toxicity after injection of 78 mg/kg single dose.

T/C=Tumor weight in treated animals divided by the tumor weight of the control animals, reported as percent value. Lower value indicates better efficacy, 0% suggests cures. <10% is considered highly active, 10 to 42% is moderately active formulation. >42% is considered inactive.

Log Kill=(T−C)/3.32 (Td), where T is the time in days for the median tumor to reach 1000 mg mass in treated animals, C is the time in days for the median tumor to reach 1000 mg in control animals and Td is the tumor volume doubling time in days. Cures (tumor free animals) are excluded from (T−C) calculations.

Example 1 demonstrates that a composition of this invention exhibited reduced toxicity and enhanced efficacy compared to a prior art composition and could be administered by IV bolus injection.

EXAMPLES 2–4

The milling procedure described in Example 1 was repeated except that the ratio of Tween 80 to Span 80 was 2:1. The resulting average particle size was 297 nm.

The milling procedure described in Example 1 was repeated except that the ratio of Tween 80 to Span 80 was 1:1. The resulting average particle size was 380 nm.

The milling procedure described in Example 1 was repeated except that the surface modifier was a 1:1 ratio of Tween 60 and Span 60. The resulting average particle size was 301 nm.

Stable pipsulfan nanoparticles were also prepared using bovine serum albumin as the surface modifier.

EXAMPLES 5–7 Nanoparticulate Camptothecin

EXAMPLE 5

Approximately 60 mL of precleaned zirconium oxide beads (1 mm) were placed in a 120 mL wide mouth round amber bottle. To it was added 0.35 g of Tetronic 908 (BASF) followed by 0.35 g of Camptothecin (Sigma Chemicals, 95% pure). To the above mixture, 35 mL of water for injection (Abbott) was added. The bottle was sealed and mounted on a roller mill. Milling was effected by rotating the bottle at 100 RPM for 7 days.

At the end of milling, an aliquot (100 μL) was checked for particle size using a Malvern Zetasizer. The particles were determined to have an average particle size of 240 nm.

EXAMPLE 6

Example 5 was repeated except that the Tetronic 908 was replaced by polyvinyl alcohol (MW 30 to 70K). The final particle size was 256 nm.

EXAMPLE 7

Example 5 was repeated except that Tetronic 908 was replaced by gum acacia. The final particle size was 298 nm.

Nanocamptothecin formulations were evaluated for efficacy in two murine tumor models, i.e., Mammary Adenocarcinoma #16/C and Pancreatic Ductal Adenocarcinoma #03. The antitumor activity was assessed by monitoring tumor weight from experimental and control animals.

1. Efficacy Studies in Pancreatic Ductal Adenocarcinoma #03:

| Example | Route | Dose mg/kg | Wt % Loss | Drug Deaths | T/C % |
|---|---|---|---|---|---|
| Control B | SC | 60 | −24.1 | 6/6 | — |
| | SC | 40.2 | −21.8 | 5/5 | — |
| | SC | 26.7 | −18.2 | 5/5 | — |
| | SC | 18 | −10.9 | 1/5 | 62 |
| 6 | IV | 83.1 | −16.7 | 1/4 | 14 |
| | IV | 78.2 | −14.6 | 1/4 | 55 |
| | IV | 48.6 | −8.3 | 0/4 | 0 |
| | IV | 24.3 | −4.2 | 0/4 | 18 |
| PVA Control | IV | — | +6.3 | 0/4 | 100 |
| 7 | IV | 93.5 | −16.7 | 1/4 | 7 |
| | IV | 46.8 | −14.6 | 0/4 | 17 |
| | IV | 23.4 | −8.3 | 0/4 | 11 |
| Cum Acacia Control | IV | — | 0.0 | 0/4 | 60 |

The Control B formulation consisted of 1% coarse camptothecin in 3% ethanol, and 1% Tween 20. Control B could only be administered subcutaneously and even at the lowest SC dose (18 mg/kg) was inactive. Control B was toxic to 1/5 animals tested. In contrast, doses of the nanocamptothecin formulations of this invention ranging from 24–93 mg/kg were administered intravenously (IV) and were shown to be safe and efficacious.

2. Efficacy Studies in Mammary Adenocarcinoma #16/C Murine Tumor Model

| Example | Route | Dose mg/kg | % Wt Loss | Drug Deaths | T/C % |
|---|---|---|---|---|---|
| Control B | SC | 60 | −23.5 | 5/5 | — |
| | SC | 30 | −20.9 | 5/5 | — |
| | SC | 15 | −18.3 | 3/5 | 14** |
| 5 | IV | 65 | −17.4 | 0/5 | 23 |
| | IV | 33 | −18.7 | 1/5 | 33 |
| | IV | 16 | −2.2 | 0/5 | 63 |
| T908 Control | IV | — | +4.3 | 0/2 | 100 |
| 6 | IV | 65 | −21.7 | 5/5 | — |
| | IV | 33 | −15.7 | 0/5 | 100 |
| PVA Control | IV | — | +4.3 | 0/2 | 100 |

**% T/C for the control animals was determined from the surviving animals, N = 2.

The T908 and PVA controls consisted of 1% aqueous solutions of the respective surface modifiers. The Control B was injected subcutaneously, and it was toxic at all doses tested. Efficacious doses of the nanocamptothecin formulations of this invention were administered intravenously.

3. Blood and Tumor Clearance

To determine if the increased efficacy was related to alterations in pharmacokinetic properties, blood clearance and tumor distribution were studied in the Mammary adenocarcinoma #16/C murine tumor model.

Tumor bearing mice were injected via the tail vein with 10 mg/ml of camptothecin formulated as described in Examples 5 and 6 and a control which was 5 mg/ml camptothecin solubilized by the addition of 0.1N NaOH. At various times after injection, i.e., 5 min., 30 min., 60 min., 2 hrs., 4 hrs., 8 hrs., 16 hrs., 24 hrs. and 48 hrs., animals were euthanized and a blood sample was collected and the tumor excised. Concentrations of drug samples were quantified using HPLC. Results show that the compositions of this invention affect the clearance of the drug from the circulating pool of blood and the tumor.

| | T½ Blood and Tumor | |
|---|---|---|
| Formulation | Blood | Tumor |
| Example 6 | 18 hrs. | >48 hrs. |
| Example 5 | 13 hrs. | >48 hrs. |
| Control | 1.6 hrs. | 13.5 hrs. |

When formulated in accordance with this invention, the elimination half-life and the residence time of camptothecin in the tumor were prolonged significantly. It was concluded that pharmacokinetic parameters of the nanoparticulate formulation of camptothecin are directly related to the improved performance of the drug.

EXAMPLES 8–10 Nanoparticulate Etoposide

EXAMPLE 8

Example 5 was repeated except that 1.7 g of etoposide was combined with 1.7 g of PVA and the milling time was 14 days. The final particle size was 310 nm. The particles were stable in acid and plasma.

EXAMPLE 9

Example 8 was repeated except that the PVA was replaced by Pluronic F-108 (BASF). The final particle size was 312 nm. The particles were stable in acid and plasma.

EXAMPLE 10

Etoposide (2%) was milled in sterile water for 7 days. A 1:1 mixture of the milled slurry was prepared with 2% Pluronic F127 solution. The mixture was vortexed before measuring particle size. The final size was 277 nm. The slurry was stable in simulated gastric fluid, PBS (pH 7.4) and rat plasma.

EFFICACY STUDIES

Nanoetoposide formulations were evaluated in two separate efficacy studies in pancreatic ductal adenocarcinoma #03 (PANC #03). Control C was a 2% non-aqueous etoposide solution prepared using the formula described on pages 741–743 of the 46th Edition of the Physicians' Desk Reference. As described above, antitumor activity was assessed by monitoring tumor weight from experimental and control animals. These studies demonstrate that the etoposide compositions of this invention provide a means to deliver high doses of the drug without evidence of severe toxic reaction.

1. Efficacy Studies for Nanoetoposide in PANC #03 Murine Tumor Model

| Example | Route | Dose mg/kg | % Wt Loss | Drug Deaths | T/C % |
|---|---|---|---|---|---|
| Control C | IV | 120 | −24.0 | 0/5 | 4.0 |
| | IV | 75 | −4.0 | 0/5 | 20.0 |
| 7 | IV | 160 | −12.0 | 0/5 | 18.0 |
| | IV | 100 | 0.0 | 0/5 | 32.0 |
| | IV | 62 | 2.0 | 0/5 | 42.0 |
| 8 | IV | 160 | −12.0 | 0/5 | 26.0 |
| | IV | 100 | +2.0 | 0/5 | 35.0 |
| | IV | 62 | +4.0 | 0/5 | 35.0 |
| 9 | IV | 170 | −18.5 | 1/5 | 16 |
| | IV | 85 | −2.0 | 0/5 | 35 |
| | IV | 43 | +2.5 | 0/5 | 41 |

EXAMPLES 11–16 Nanoparticulate Taxol

EXAMPLE 11

Approximately 18 mL of precleaned zirconium oxide media (1 mm) was added to a 30 mL amber jar. To it was added 240 mg of taxol (Sigma Chemicals) and 180 mg of Tween 20. Finally, 12 mL of water for injection was added to the jar, it was sealed and mounted on a roller mill for 11 days. The final particle size was 327 nm. The formulation was stable when exposed to PBS (pH 7.4) and rat plasma.

EXAMPLE 12

Example 11 was repeated except that the Tween 20 was replaced with PVA (MW 30 to 70 k). The final particle size was 365 nm.

The above samples were evaluated in efficacy studies in mice bearing early stage mammary adenocarcinoma #16/C. The antitumor activity was assessed by comparing tumor weights of taxol treated animals with the tumor weights of untreated animals. The toxicity was assessed by dose ranging studies with death and weight loss as end points. All samples were injected IV.

| Example | Dose mg/kg | % Wt Loss | Deaths | Median Tumor on Day 11 | T/C % |
|---|---|---|---|---|---|
| Control D | — | +6.1 | — | 1539 mg | — |
| Example 11 | 108.5 | −1.5 | 0/5 | 1528 | 13 |
| Example 12 | 108.5 | −3.0 | 0/5 | 201 | 99 |

A control sample of taxol (NCI) was not available. However, a single dose of taxol formulated in Cremophore EL causes immediate deaths at 25 mg/kg total dose. However, taxol formulated in compositions of this invention could be injected at a dose of 88 mg/kg with no apparent adverse effects.

A taxol suspension prepared in a manner similar to Example 11 was treated separately with several surface modifiers. After addition of the new surface modifier the mixture was vortexed and evaluated for particle size and fluid stability. All the suspensions contained 1% taxol and 0.75% Tween 20. The results are as follows.

| Example/ Surface Modifier | Concentration % | Size (nm) | Fluid Stability | |
|---|---|---|---|---|
| | | | PBS | Rat Plasma |
| 13 CTAC | 0.25 | 364 | OK | Flocculation |
| 14 AOT | 0.25 | 322 | SA* | SA |
| 15 F68 | 0.5 | 297 | SA/OK | SA/OK |

-continued

| Example/ Surface Modifier | Concentration % | Size (nm) | Fluid Stability PBS | Rat Plasma |
|---|---|---|---|---|
| 16 T908 | 0.5 | 313 | SA/OK | SA/OK |

*SA = Slight Aggregation

EXAMPLES 17–18 Nanoparticulate WIN 59075

Approximately 60 mL of precleaned zirconium oxide (1 mm) media was transferred into a 4 oz amber jar. It was followed by addition of 1.5 g of WIN 59075 and 28.5 mL of water for injection. The jars were sealed, loaded onto a roller mill and cascaded at 95 RPM for 48 hrs. PCS analysis determined the particle size to be 322 nm, however, the presence of larger particles was suggested. Milling was continued for 5 additional days.

Studies were conducted by mixing 0.5 mL of the WIN 59075 slurry prepared above with 0.5 mL of 6% surface modifier solutions. The final concentration of the drug was 2.5% and that of the surface modifiers was 3%. The surface modifier stabilized nanosuspensions of WIN 59075 were then treated with either PBS (pH 7.0) or 0.1N HCl (pH 1). Optical microscopic observations were made to determine fluid stability. The results are as follows;

| Example | Surface Modifier | Stability pH 1 | pH 7 | Human Plasma |
|---|---|---|---|---|
| 17 | PVP (12K) (BASF) | Fine | Fine | Fine |
| 18 | Gum Acacia (Aldrich) | — | SA/OK | SA/OK |

It was concluded that stable nanoparticles of WIN 59075 could be prepared.

EXAMPLES 19–22 Nanoparticulate SR 4889

7.5 mL of precleaned zirconium oxide media (1 mm) was transferred into a 15 mL amber jar along with 18.75 mg of SR 4889 and 3.75 mL of water. After 11 days of milling the nanosuspension was separated from the media. To each of the 100 μL aliquots of the suspension, 100 μL of a surfactant solution (2%) was added giving a final concentration of 0.25% drug and 1% surfactant. The mixture was vortexed and analyzed for particle size. Fluid stability was assessed microscopically by mixing 10 μL of the suspension with 90 μL of rat plasma. The results are as follows:

| Example | Surface Modifier | Particle Size (nm) | Fluid Stabilty Rat Plasma |
|---|---|---|---|
| 19 | PVP (12K) | 134 | Fine |
| 20 | Gum Acacia | 344 | SA/OK |
| 21 | Tween 80 | 128 | Fine |
| 22 | T908 | 130 | Aggregates |

EXAMPLE 23 Nanoparticulate Retinoic Acid 30 mL of precleaned zirconium oxide media was transferred to a 60 mL amber jar. To it was added 1 g of transretinoic acid (Sigma), 470 mg of tyloxapol and 15 mL of water. The mixture was milled on a roller mill for 15 days. The final particle size was 140 nm. The nanosuspension was stable when exposed to either rat plasma or simulated gastric fluid.

The invention has been described in detail with particular reference to certain preferred embodiments thereof, but it will be understood that variations and modifications can be effected within the spirit and scope of the invention.

What is claimed:

1. Particles consisting essentially of 99.9% by weight of a crystalline medicament useful in treating cancer susceptible to treatment with said medicament, said medicament having a solubility in water of less than 10 mg/ml, and having a non-crosslinked surface modifier adsorbed on the surface thereof in an amount of 0.1–90% by weight and sufficient to maintain an average effective particle size of less than 1000 nm, wherein said medicament is selected from the group consisting of alkylating agents selected from the group consisting of alkylating agents having a bis-(2-chloroethyl)-amine group, alkylating agents having a substituted aziridine group, alkyl sulfonates, and N-alkyl-N-nitrosoureas; antimetabolites; natural products selected from the group consisting of vinca alkaloids, epipophylotoxins, adriamycine, daunomycine, doctinomycine, daunorubicin, doxorubicin, mithramycin, bleomycin, mitomycin, enzymes, biological response modifiers, camptothecin, taxol and retinoids; hormones and antagonists: radiosensitizers; platinum coordination complexes; anthracenediones; and adrenocortical suppressants.

2. The particles of claim 1 having an average effective particles size of less than 400 nm.

3. The particles of claim 1 having an average effective particle size of less than 300 nm.

4. The particles of claim 1 wherein said surface modifier is present in an amount of 1 to 75% by weight.

5. The particles of claim 1 wherein said anticancer agent is selected from the group consisting of piposulfan, piposulfam, camptothecin, etoposide, taxol, 1,2,4-benzotriazin-3-amine 1,4-dioxide, 1,2,4-benzotriazin-7-amine 1,4-dioxide and retinoic acid.

6. The particles of claim 1 wherein said surface modifier is selected from the group consisting of polyvinyl alcohol, a tetrafunctional block copolymer derived from sequential addition of ethylene oxide and propylene oxide to ethylenediamine, gum acacia, a block copolymer of ethylene oxide and propylene oxide, a polyoxyethylene sorbitan fatty acid ester, and a sorbitan ester of a fatty acid.

7. The particles of claim 1 wherein said anticancer agent is taxol and said surface modifier comprises a polyoxyethylene sorbitan fatty acid ester.

8. An anticancer composition comprising the particles of claim 1.

9. A method of treating a mammal comprising administering to the mammal an effective amount of the anticancer composition of claim 8.

10. In a method of treating a mammal comprising administering to the mammal an effective amount of an anticancer agent, the improvement wherein the efficacy of said anticancer agent is increased by administering said anticancer agent in the form of the particles of claim 1.

11. In a method of treating a mammal comprising administering to the mammal an effective amount of an anticancer agent, the improvement wherein the toxicity of said anticancer agent is reduced by administering said anticancer agent in the form of the particles of claim 1.

12. The particles of claim 1 wherein said surface modifier is a surfactant.

13. The particles of claim 1 wherein said surface modifier is a nonionic surfactant.

14. The particles of claim 1 wherein said surface modifier is an anionic surfactant.

15. The particles of claim 1 wherein said surface modifier is selected from the group consisting of gelatin, casein, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, polyvinyipyrrolidone, poloxomers, tyloxapol, poloxamines, dextran, a dioctyl ester of sodium sulfosuccinic acid, sodium lauryl sulfate, an alkyl aryl polyether sulfonate, a mixture of sucrose stearate and sucrose distearate, hexyldecyl trimethyl ammonium chloride, bovine serum albumin and $C_{18}H_{37}CH_2(CON(CH_3)CH_2(CHOH)_4CH_2OH)_2$.

16. The particles of claim 1 wherein said surface modifier is present in an amount of 10 to 60% by weight based on the total weight of the dry particle.

17. The particles of claim 1 wherein said surface modifier is present in an amount of 10 to 30% by weight based on the total weight of the dry particle.

* * * * *

UNITED STATES PATENT AND TRADEMARK OFFICE
CERTIFICATE OF CORRECTION

PATENT NO.   : 5,399,363                                        Page 1 of 1
DATED        : March 21, 1995
INVENTOR(S)  : Gary G. Liversidge, Elaine Liversidge and Pramod P. Sarpotdar It is certified that error appears in the above-identified patent and that said Letters Patent is hereby corrected as shown below:

Column 14,
Line 7, delete "99.9%" and insert -- 99.9-10% --.

Signed and Sealed this

Twenty-fifth Day of April, 2006

JON W. DUDAS
*Director of the United States Patent and Trademark Office*